(12) United States Patent
Holden et al.

(10) Patent No.: US 12,408,822 B2
(45) Date of Patent: Sep. 9, 2025

(54) DEVICES, SYSTEMS, AND METHODS FOR AN INSTRUMENT ACCESSORY

(71) Applicant: Boston Scientific Scimed, Inc., Maple Grove, MN (US)

(72) Inventors: Méabh Holden, Dublin (IE); Richard Crawford, Galway (IE); Enda Connaughton, Galway (IE); Martin L. Fawdry, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 269 days.

(21) Appl. No.: 17/196,193

(22) Filed: Mar. 9, 2021

(65) Prior Publication Data
US 2021/0282627 A1 Sep. 16, 2021

Related U.S. Application Data

(60) Provisional application No. 62/987,482, filed on Mar. 10, 2020.

(51) Int. Cl.
*A61B 1/00* (2006.01)
*A61B 1/273* (2006.01)
(Continued)

(52) U.S. Cl.
CPC ...... *A61B 1/00154* (2013.01); *A61B 1/00082* (2013.01); *A61B 1/273* (2013.01);
(Continued)

(58) Field of Classification Search
CPC . A61B 1/00082; A61B 1/00154; A61B 1/273; A61B 1/00135; A61B 1/00142;
(Continued)

(56) References Cited

U.S. PATENT DOCUMENTS

| 4,224,929 A | * | 9/1980 | Furihata | A61B 1/00098 600/116 |
| 5,361,752 A | * | 11/1994 | Moll | A61B 17/0281 604/908 |

(Continued)

FOREIGN PATENT DOCUMENTS

EP 1063915 A1 1/2001

OTHER PUBLICATIONS

Meseeha M, Attia M. Endoscopic Retrograde Cholangiopancreatography. [Updated Aug. 11, 2020]. In: StatPearls [Internet]. Treasure Island (FL): StatPearls Publishing; Jan. 2021.

(Continued)

*Primary Examiner* — Ryan N Henderson
(74) *Attorney, Agent, or Firm* — Seager, Tufte & Wickhem, LLP

(57) ABSTRACT

The present disclosure, in its various aspects, is directed to instrument accessory devices, implementation methods, and related delivery systems. Embodiments according to the present disclosure, including as described herein, may increase the effectiveness and efficiency of endoscopy procedures, such as ERCP. In one example, an embodiment includes an instrument accessory device with an expandable member, the device configured to receive an instrument through an instrument lumen, wherein the expandable member comprises an aperture on the inner surface and outer surface, and the outer surface is in fluid communication with the inner surface.

6 Claims, 7 Drawing Sheets

(51) Int. Cl.
*A61B 17/30* (2006.01)
*A61M 25/10* (2013.01)

(52) U.S. Cl.
CPC .................. *A61B 2017/306* (2013.01); *A61M 2025/1061* (2013.01)

(58) Field of Classification Search
CPC .................. A61B 1/0008; A61B 1/31; A61M 2025/1043; A61M 2025/1045; A61M 2025/1054; A61M 2025/1056; A61M 2025/1061; A61M 2025/107
See application file for complete search history.

(56) References Cited

U.S. PATENT DOCUMENTS

| | | | | |
|---|---|---|---|---|
| 5,716,321 A * | 2/1998 | Kerin | ..................... | A61B 90/50 604/528 |
| 5,938,585 A * | 8/1999 | Donofrio | ........... | A61B 1/00082 600/116 |
| 6,277,065 B1 * | 8/2001 | Donofrio | ........... | A61B 1/00082 600/116 |
| 7,833,150 B2 * | 11/2010 | Yamamoto | ......... | A61B 1/00082 600/116 |
| 9,986,897 B2 * | 6/2018 | Inoue | ................ | A61B 1/00098 |
| 10,441,143 B2 * | 10/2019 | Inoue | ................ | A61B 1/00154 |
| 11,071,534 B2 * | 7/2021 | Piskun | ............... | A61B 17/0218 |
| 11,241,560 B2 * | 2/2022 | Piskun | ................. | A61B 1/0051 |
| 2004/0127767 A1 | 7/2004 | Fleener et al. | | |
| 2005/0234293 A1 * | 10/2005 | Yamamoto | ......... | A61B 1/00149 600/102 |
| 2008/0249356 A1 * | 10/2008 | Motai | ................ | A61B 1/00082 600/114 |
| 2010/0049001 A1 * | 2/2010 | Yamane | ................ | A61B 1/015 600/159 |
| 2011/0208003 A1 * | 8/2011 | Yamane | ................... | A61B 1/12 600/159 |
| 2012/0238815 A1 * | 9/2012 | Komi | ................ | A61B 1/00098 600/114 |
| 2014/0024897 A1 * | 1/2014 | Inoue | ................ | A61B 1/00154 600/114 |
| 2015/0105621 A1 * | 4/2015 | Farhadi | .............. | A61B 1/00135 600/115 |
| 2016/0081537 A1 * | 3/2016 | Farhadi | .............. | A61B 1/00154 600/115 |
| 2017/0065155 A1 * | 3/2017 | Farhadi | .............. | A61B 1/00154 |
| 2018/0185018 A1 * | 7/2018 | Piskun | ................ | A61B 1/3132 |
| 2018/0249897 A1 * | 9/2018 | Inoue | ................ | A61B 1/00098 |
| 2018/0264239 A1 * | 9/2018 | Piskun | ................... | A61B 17/22 |
| 2019/0246883 A1 * | 8/2019 | Bashour | ............. | A61B 1/00082 |

OTHER PUBLICATIONS

International Search Report and Written Opinion for the International Patent Application No. PCT/US2021/021481, mailed Jun. 15, 2021, 21 pages.

* cited by examiner

DEVICES, SYSTEMS, AND METHODS FOR AN INSTRUMENT ACCESSORY

PRIORITY

The present application is a non-provisional of and claims the benefit of priority under 35 USC § 119 to, U.S. Provisional Application Ser. No. 62/987,482, filed Mar. 10, 2020, the disclosure of which is herein incorporated by reference in its entirety.

FIELD

The present disclosure pertains to medical devices. More particularly, the present disclosure pertains to instrument accessory devices and related systems and methods, particularly as may increase the effectiveness and efficiency of endoscopy procedures.

BACKGROUND

Endoscopes, for example, are used in medical procedures to examine and treat conditions within the digestive tract. Endoscopic Retrograde Cholangiopancreatography (ERCP) is used to examine and treat issues in the common bile duct and pancreatic ducts. In some procedures, cannulation of the bile duct can be difficult, with movement in the duodenum creating positioning and stabilization of the endoscope hard to achieve. Peristaltic movements in the duodenum can require medicating the patient to suppress such movements. Further, the tightly contracted musculature of the duodenal papilla requires high levels of precision to maneuver endoscope through the papilla opening. Consequently, the effectiveness and efficiency of the procedure may become compromised, and the inability to cannulate the common bile duct may result in a failed ERCP.

It is with the above considerations in mind that the improvements of the present disclosure may be useful.

SUMMARY

The present disclosure, in its various aspects, is directed generally to instrument accessory devices, implementation methods, and related systems. Embodiments according to the present disclosure, including those described herein, may increase particularly the effectiveness and efficiency of procedures used for the examination and treatment of conditions within the body, e.g., cannulation of the bile duct during ERCP.

In an aspect, an instrument accessory device may include an expandable member having a proximal end and a distal end extending along a longitudinal axis, an inner layer having an inner surface defining an inner diameter of the expandable member, and an outer layer disposed about the inner layer and having an outer surface defining an outer diameter of the expandable member. The inner surface may define an instrument lumen extending from the proximal end toward the distal end of the expandable member. The instrument lumen may be configured to receive an instrument therethrough. The expandable member may comprise an aperture that extends radially outward from the instrument lumen to an exterior of the expandable member beyond the outer diameter. The instrument lumen may be in fluid communication with the exterior of the expandable member the via the aperture. Moreover, the aperture may provide an unobstructed view between the instrument lumen and the exterior of the expandable member.

In various embodiments described here or otherwise, the instrument lumen may be configured to receive an instrument. The instrument may be an endoscope or a duodenoscope. The instrument lumen may be configured to maintain frictional contact with the instrument when the expandable member is in a collapsed condition. The inner layer and the outer layer may define inner and outer walls of a chamber that may be pressurized. The instrument accessory device may include an inflation lumen that extends through the outer layer of the expandable member and into the chamber. The inner layer may comprise a material configured to maintain frictional contact with an instrument. The outer layer may comprise a compliant elastic material.

In an aspect, an endoscopic system may comprise a duodenoscope. The system may include an endoscope accessory device disposable about the instrument. The endoscope accessory may comprise an expandable member having a proximal end, a distal end, a longitudinal axis, an inner layer having an inner surface defining an inner diameter, and an outer layer disposed about the inner layer and having an outer surface defining an outer diameter. The instrument lumen may extend from the proximal end toward the distal end of the expandable member. The instrument lumen may be configured to receive an instrument therein. The expandable member may comprise an aperture that extends radially outward from the instrument lumen to an exterior of the expandable member such that the instrument lumen is in fluid communication with the exterior of the expandable member the via the aperture. The instrument lumen of the expandable member may be configured to slidingly receive at least a distal portion of the duodenoscope.

In various embodiments described here or otherwise, the expandable member may be configured to maintain frictional contact with the endoscope. The inner surface may comprise a body (e.g., a defined structure). The system may comprise a vacuum source. The expandable member may be placed in an expanded condition, stabilizing an instrument within a patient. The expandable member may be pneumatically, electrically, or mechanically expandable. The system may further comprise a fluid which is injected into the expandable member.

In an aspect, a method of performing an endoscopy may comprise connecting an instrument accessory device to an instrument, the instrument accessory device comprising an expandable member and an instrument lumen. The expandable member may comprise an aperture that extends radially outward from the instrument lumen to an exterior of the expandable member such that the instrument lumen is in fluid communication with the exterior of the expandable member the via the aperture. The instrument and instrument accessory device may be inserted into a patient. The expandable member may be expanded within the patient to an expanded state.

In various embodiments described here or otherwise, the method may also comprise applying a vacuum with the instrument. The expandable member may be expanded within the patient expanding an outer diameter such that the expandable member engages a patient lumen and stabilizes the instrument within the patient. Expanding the expandable member may comprise injecting a gas or liquid into the expandable member. The outer surface may be expandable to fit a body cavity. The instrument may comprise a duodenoscope. The instrument accessory device may comprise an inflation lumen extending from the proximal end of the instrument accessory device to an interior chamber of the expandable member. The aperture may be positioned such that the instrument interacts with a body cavity of the patient. The expandable member may be collapsed within the patient

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 1:
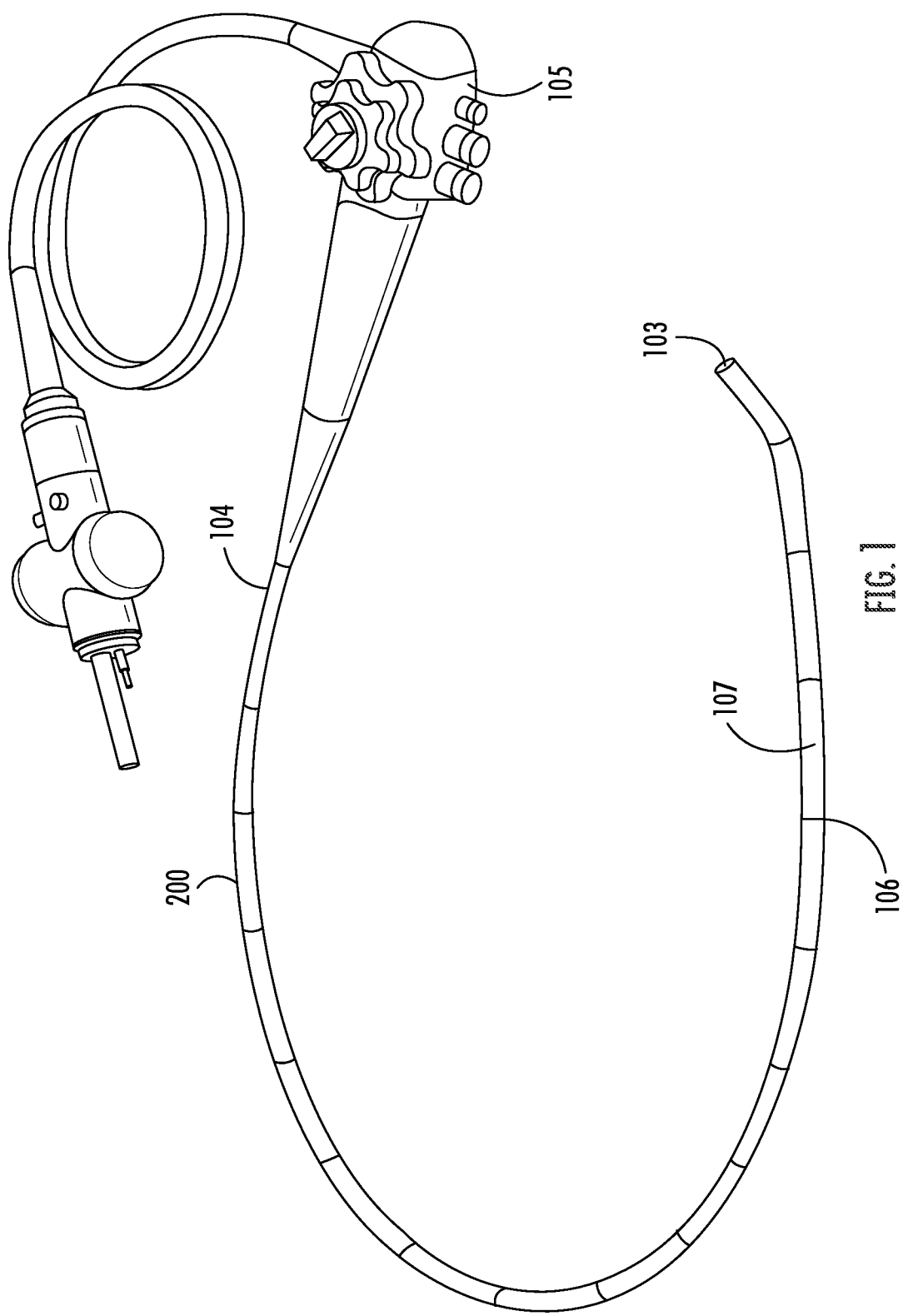
FIG. 1 illustrates an exemplary endoscope of a type described in an embodiment of the present disclosure.

It is noted that the drawings are intended to depict only typical or exemplary embodiments of the disclosure. Accordingly, the drawings should not be considered as limiting the scope of the disclosure. The disclosure will now be described in greater detail with reference to the accompanying drawings.

DETAILED DESCRIPTION

Various embodiments according to the present disclosure are described below. As used herein, "proximal end" refers to the end of a device that lies closest to the medical professional along the device when introducing the device into a patient, and "distal end" refers to the end of a device or object that lies furthest from the medical professional along the device during implantation, positioning, or delivery.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used in connection with other embodiments whether or not explicitly described unless clearly stated to the contrary.

The detailed description should be read with reference to the drawings, which are not necessarily to scale, depict illustrative embodiments and are not intended to limit the scope of the invention.

Embodiments of the present disclosure may include an instrument accessory as a device for use with an instrument. An instrument may be an endoscope, duodenoscope, colonoscope, bronchoscope, gastroscope, ureteroscope, catheter, or the like. The device may include various components and configurations. Embodiments of this disclosure may comprise a medical device system. A medical device system may include an instrument, a handle, an instrument accessory, and/or a source of inflation fluid, or the like. Embodiments of the devices and systems may be used to fill a body lumen around the instrument, during an endoscopic procedure, to enable the operator to stabilize the instrument within the body. Various embodiments described herein comprise an instrument accessory device having an expandable member about an instrument lumen that can slidingly receive an instrument. The expandable member once expanded within the body lumen may inhibit movement of the endoscope within the body lumen. In some embodiments, the inflation fluid may be a gas or a liquid. In some embodiments, the body lumen may include a lumen, organ, vessel, passage, or the like, within, e.g., the digestive system, or the like.

Endoscopic Retrograde Cholangiopancreatography (ERCP) is used to examine and treat issues in the common bile duct and pancreatic ducts. An endoscope is introduced into the patient via the mouth, through the stomach and advanced through the small intestine. The endoscope may be used to access the ampulla of Vater in order to reach the pancreatic and bile ducts. The positioning of the endoscope relative to the duodenal papilla is key to the success of the procedure, and can be made difficult by movement of the duodenum.

For various uses of endoscopes or other instruments, within various body lumens and for various purposes, such as described above, embodiments of the instrument accessory devices, systems and methods of the present disclosure may be utilized to enable the physician to perform procedures with greater precision, accuracy, and ease than without the accessory devices.

An instrument accessory device may include an expandable member. An expandable member may include an inner layer having an inner surface which may be a non-elastic material such as Nylon, PET, PTFE, Pebax®. An expandable member may include an outer layer having outer surface which may be an elastic material such as a compliant balloon, a mesh, scaffold, a braid, or the like. An expandable member may be mechanically actuated, electrically actuated, pneumatically actuated, inflated, or the like. An expandable member may transition from a collapsed configuration to an expanded configuration to occlude, stretch, establish patency, or maintain patency of a body lumen.

An instrument accessory device may have a fluid inlet that may extend through the outer surface of an expandable member. The fluid inlet may supply and remove an inflation fluid for inflating, or expanding and un-expanding or collapsing the expandable member.

In one method of performing an endoscopy, a distal end of an endoscope may be advanced through the small intestine via the mouth of a patient. Once inside the patient, the digestive system can be visually examined and the pancreatic and bile ducts may be accessed using an instrument passed through a working channel from a handle at the proximal end of the endoscope that remains outside of the body.

Referring to FIG. 1, an embodiment of a distal end of an endoscope of the type described in the present disclosure is illustrated. The endoscope 200 is one example of an instrument that can be used with an instrument accessory device described further herein. The endoscope 200 comprises a distal end 103 and a proximal end 104 with a lumen or working channel extending therethrough. A handle 105 at the proximal end 104 may be operated by a medical professional to manipulate the endoscope 200. The endoscope 200 may include cuts or channels 106 along a wall 107 of the insertion portion of the endoscope 200 in order to facilitate movement and flexibility within a patient, e.g., by operation of steering knobs at the handle 105.

Figure 2A:
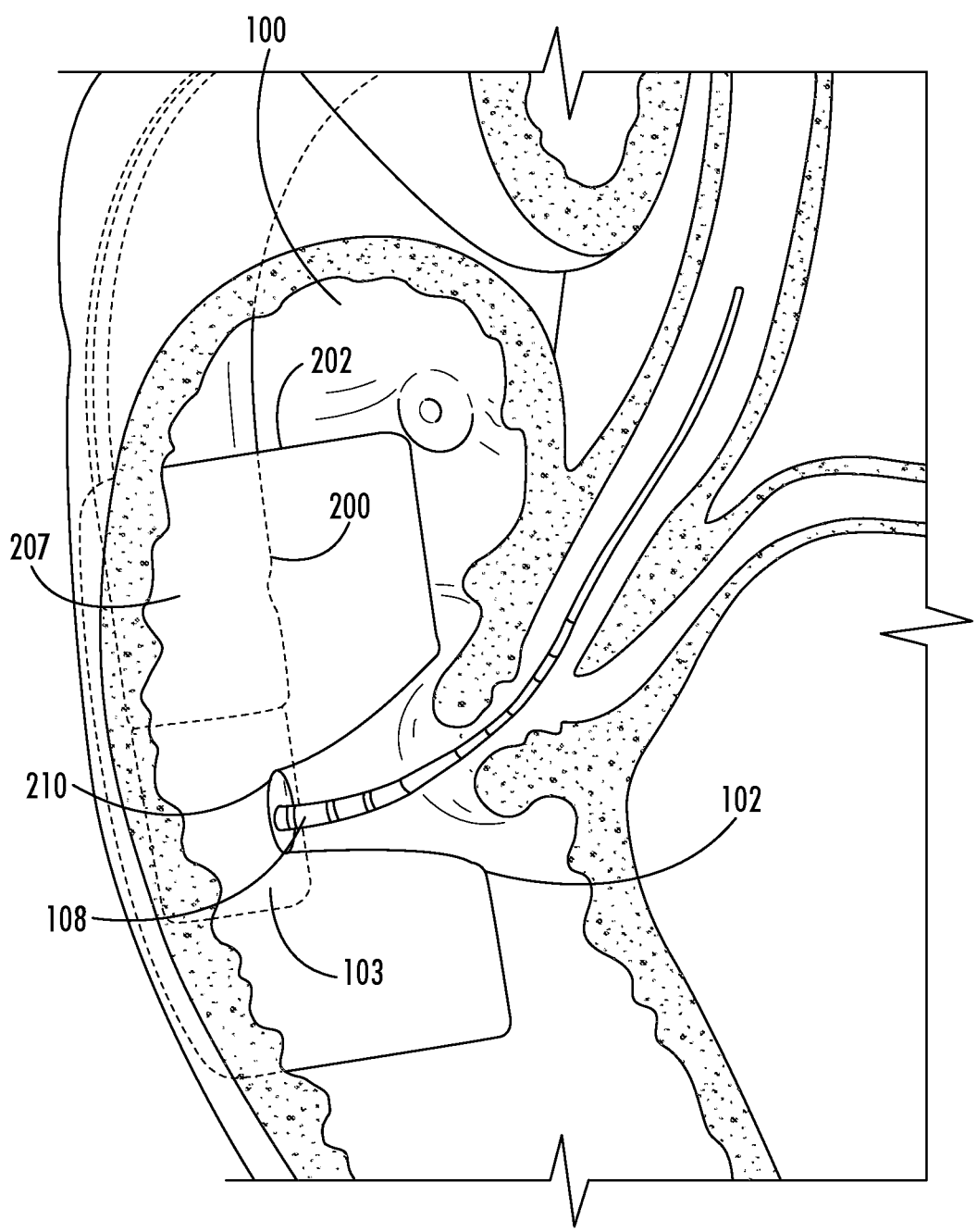
FIG. 2A illustrates a partial cross-sectional view of an endoscope system with an instrument accessory device in an expanded configuration within a duodenum and an exemplary endoscope, such as the endoscope of FIG. 1, extended therethrough, in accordance with an embodiment of the present disclosure.
Figure 2B:
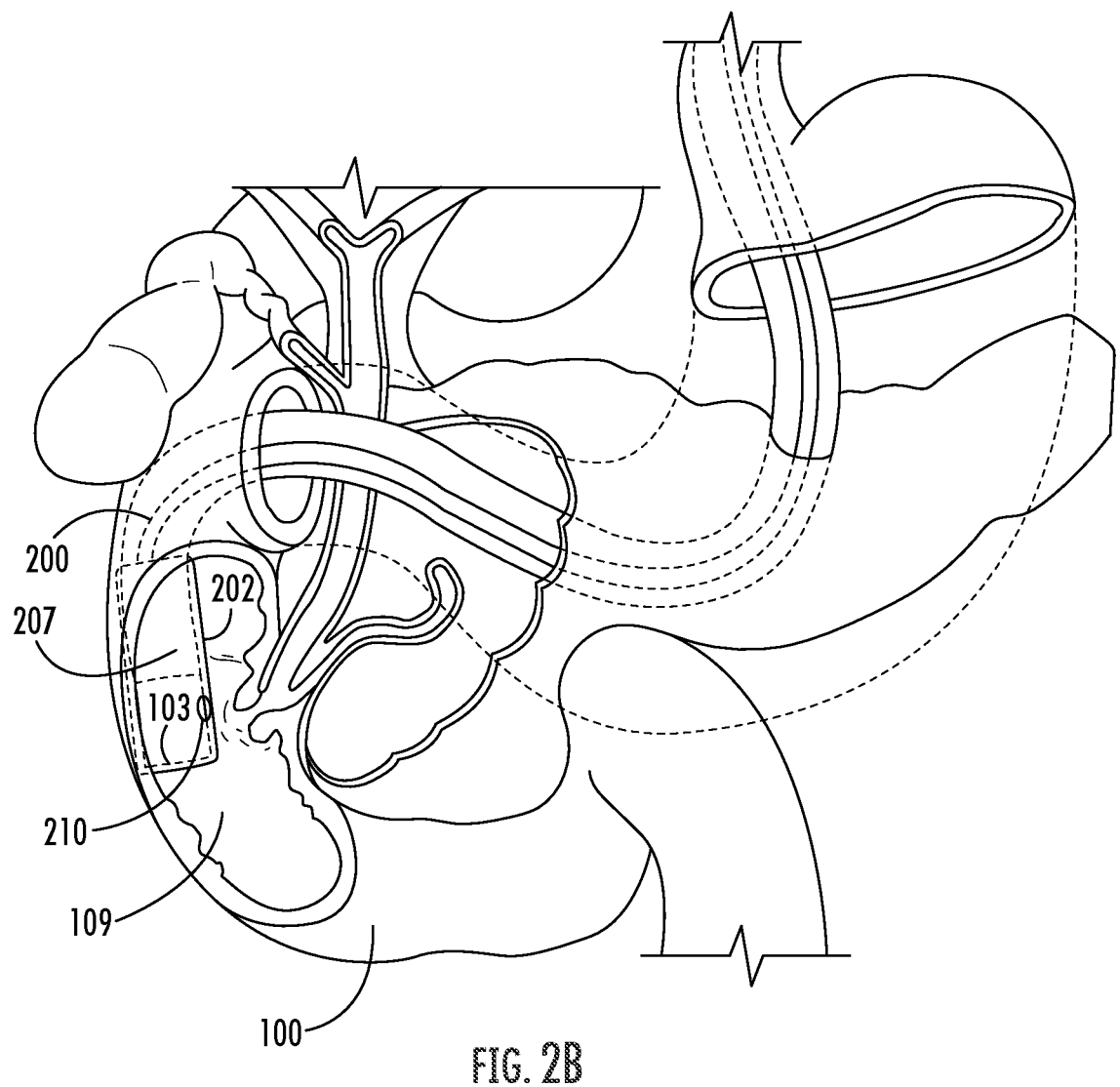
FIG. 2B illustrates a partial cross-sectional view of an endoscope system with an instrument accessory device, such as the device of FIG. 2A, in a collapsed configuration within a body and an exemplary endoscope, such as the endoscope of FIG. 1, extended therethrough, in accordance with an embodiment of the present disclosure.

Referring to FIGS. 2A and 2B, a view of an endoscopic system within the body is illustrated according to an embodiment of the present disclosure, which includes an instrument accessory device 102 slidably disposed around an endoscope 200 (e.g., the endoscope 200 of FIG. 1). The distal end 103 of the endoscope 200 and instrument accessory device 102 may be advanced through the small intestine 100, with the proximal end of the endoscope 200 remaining outside the body. When the endoscope 200 is being advanced through the body, the instrument accessory device remains disposed about the endoscope 200 by maintaining frictional contact with the endoscope 200. Once the endoscope 200 is in position, the expandable member 202 of the instrument accessory device 102 may be expanded, and a catheter 108 extended through the aperture 210. The expandable member 202 of the device may substantially fill a cross-section of the body lumen 109 while in the expanded configuration. The expandable member 202 may be transitioned from a collapsed configuration to an expanded configuration by supply of an inflation fluid through a fluid inlet extending through the outer layer of the expandable member 202. The body lumen 109, e.g., small intestine, duodenum, etc., may be substantially occluded by the expandable member 202 when the expandable member 202 is in an expanded state. The endoscope 200 may be immovable within the instrument lumen 207.

Figure 3:
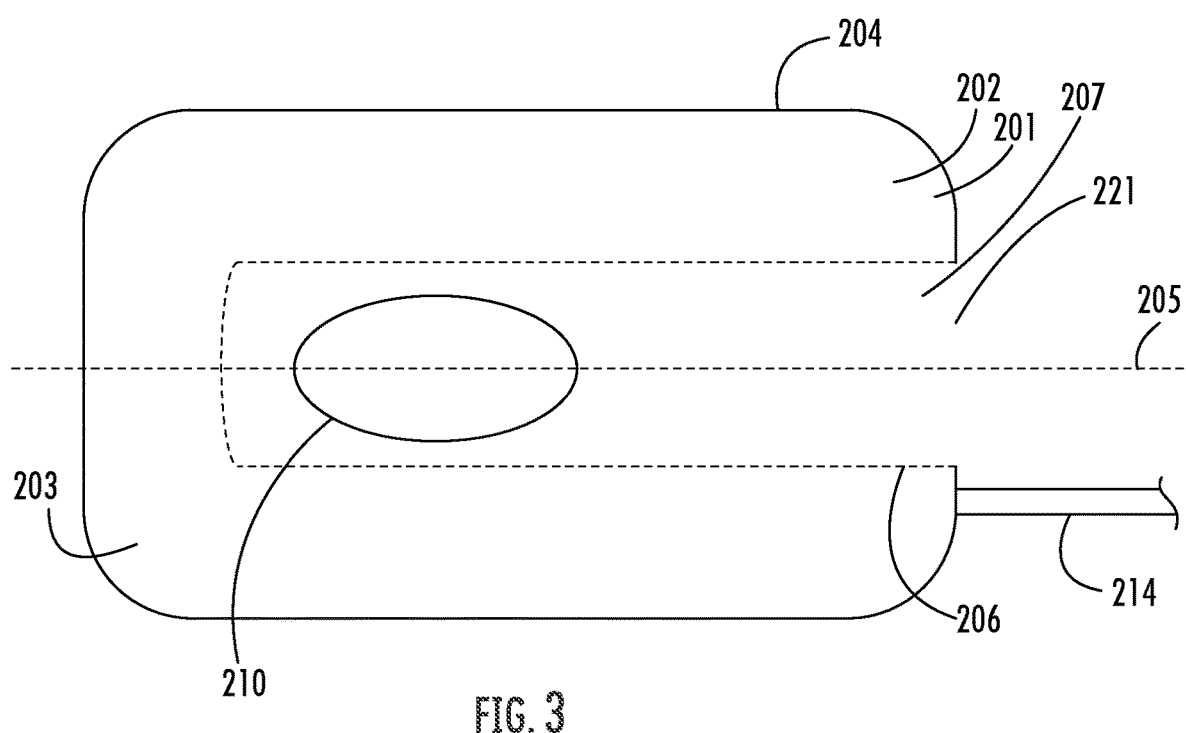
FIG. 3 illustrates a side view of an instrument accessory device in an expanded configuration, in accordance with an embodiment of the present disclosure.

Referring to FIG. 3, an instrument accessory device 102 is illustrated according to embodiments of the present disclosure. The instrument accessory device 102 includes an expandable member 202 having a proximal end 201, a distal end 203, and a longitudinal axis 205. An inner layer 206 having inner surface defines an inner diameter of the expandable member 202, extending from the proximal end 201 towards the distal end 203. The inner layer 206 defines an instrument lumen 207 having an inlet 221 at the proximal end 201 and the instrument lumen 207 extending towards the distal end 203. The instrument lumen 207 is configured to receive an instrument, e.g., the endoscope of FIG. 1, extendable through the instrument lumen 207. A fluid inlet 214 extends from the proximal end 201 of the expandable member 202.

Figure 4A:
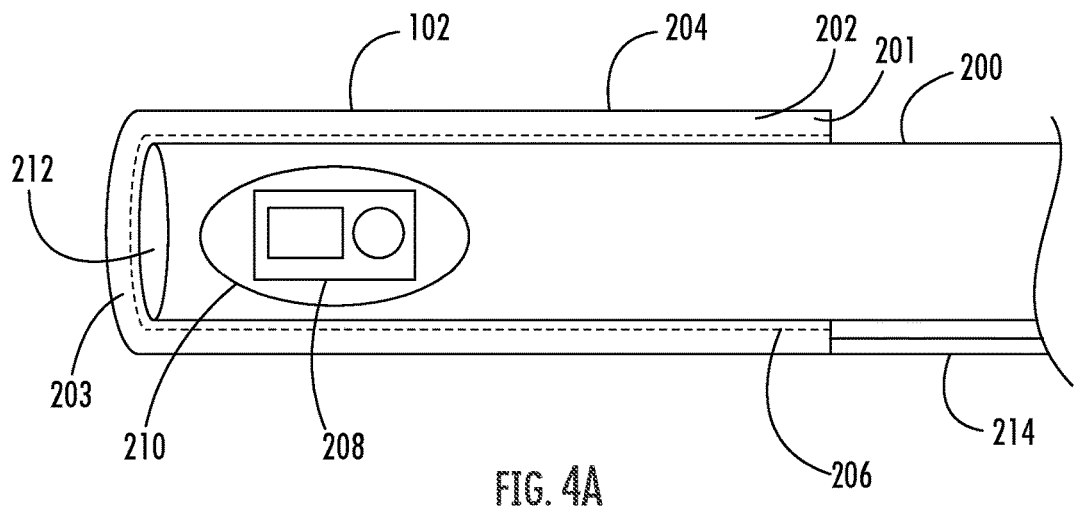
FIG. 4A illustrates a longitudinal partial cross-sectional view of the instrument accessory device of FIG. 3, in a collapsed configuration, with an inserted endoscope.
Figure 4B:
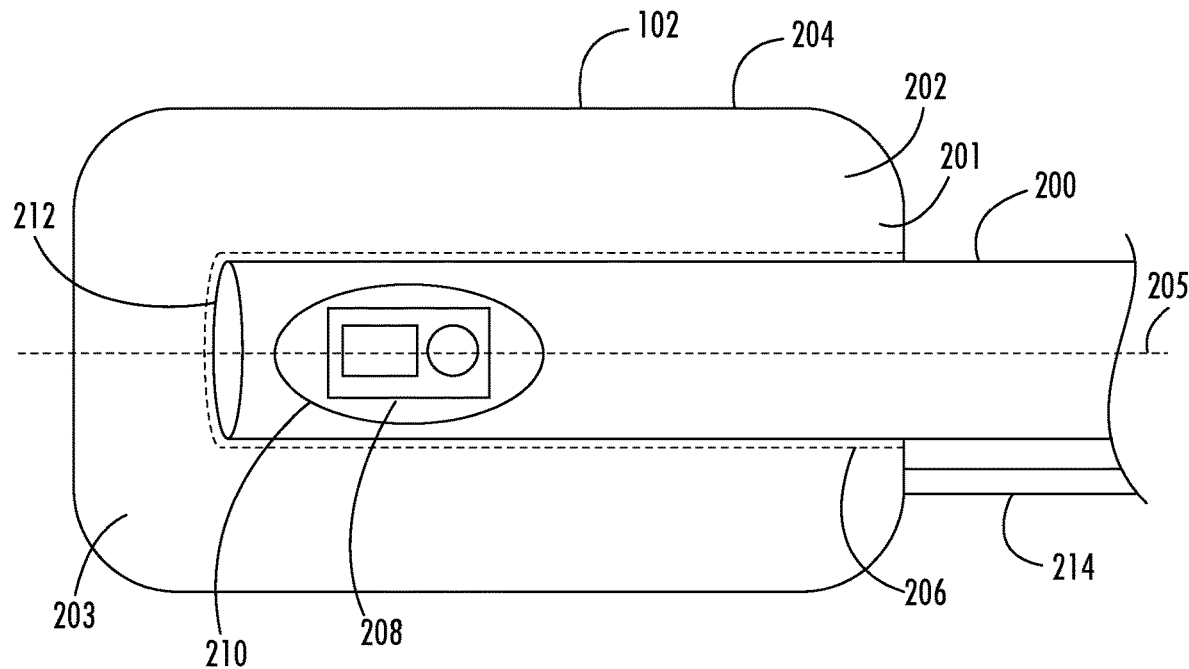
FIG. 4B illustrates a longitudinal partial cross-sectional view of the instrument accessory device of FIG. 3, in an expanded configuration, with an inserted endoscope.
Figure 5A:
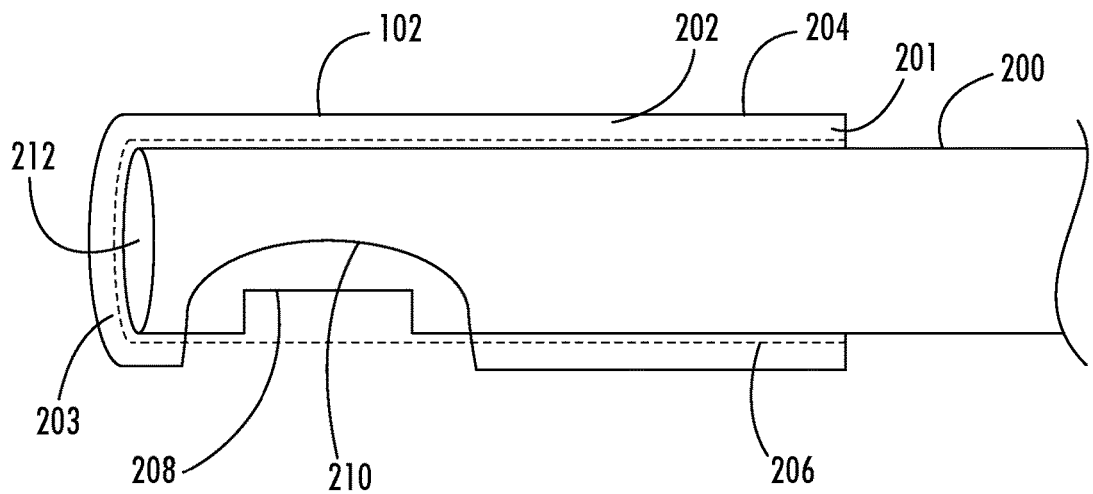
FIG. 5A illustrates a longitudinal partial cross-sectional view of the instrument accessory device of FIG. 4A, in a collapsed configuration.
Figure 5B:
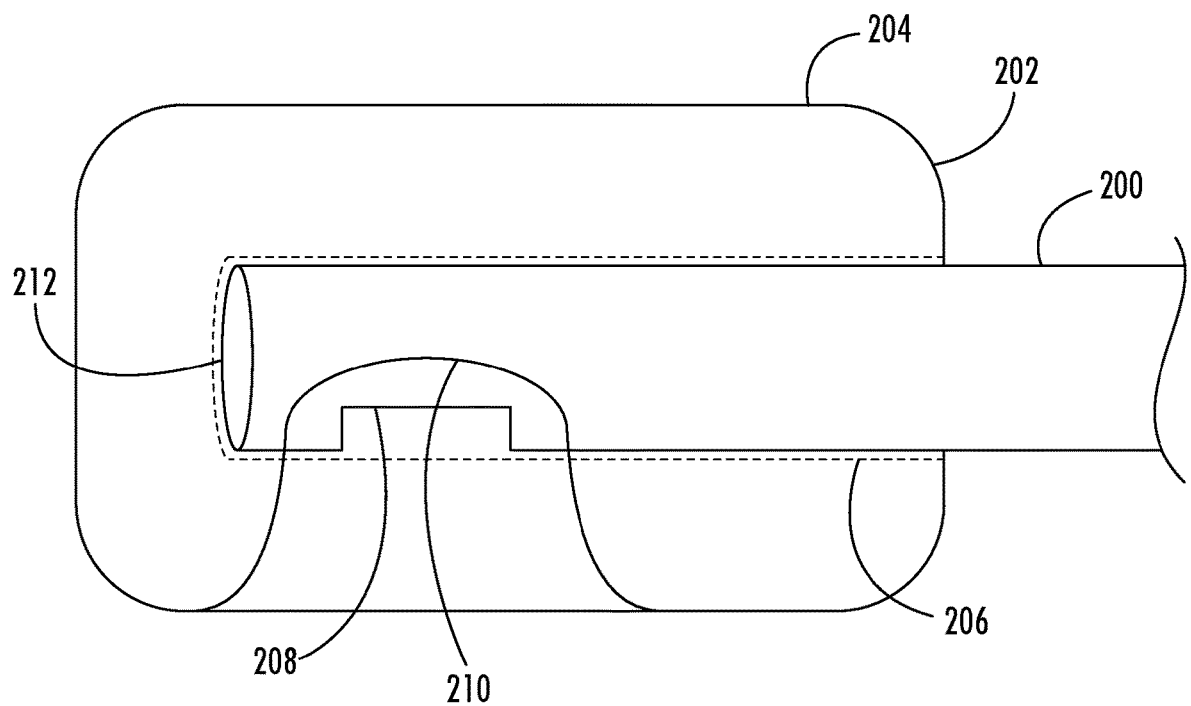
FIG. 5B illustrates a longitudinal partial cross-sectional view of the instrument accessory device of FIG. 4B, in an expanded configuration.
Figure 6A:
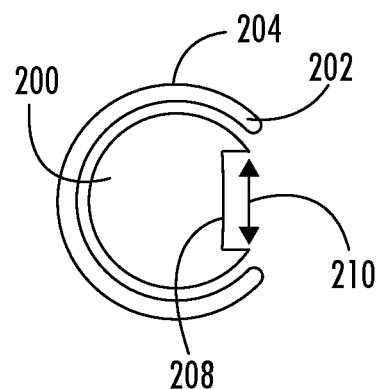
FIG. 6A illustrates a radial cross-sectional view of an instrument accessory device in a collapsed configuration.
Figure 6B:
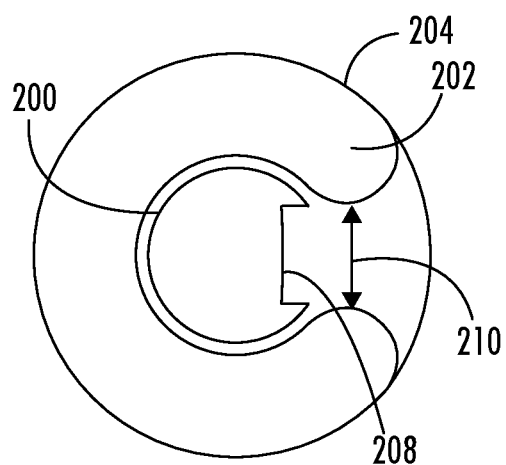
FIG. 6B illustrates a radial cross-sectional view of an instrument accessory device in an expanded configuration.

An outer layer 204 having outer surface defining an outer diameter of the expandable member 202 extends between the proximal 201 and distal 203 ends along a longitudinal axis 205. The longitudinal axis 205 of the instrument lumen 207 and the longitudinal axis 205 of the expandable member 202 may be coextensive with each other, as shown, or may be radially offset from each other (not shown). The instrument lumen 207 and the expandable member 202 may each have a center axis as the longitudinal axis 205 that may be coextensive or radially offset from each other. The accessory devices shown in FIGS. 3, 4A, and 4B include fluid inlet 214 having a proximal end (not shown), a distal end, and an inflation lumen therethrough. The distal end of the fluid inlet 214 extends to the outer layer 204 of the expandable member 202. An inner lumen of the fluid inlet 214 is in fluid communication with an interior chamber of the expandable member 202. An aperture 210 is positioned between the proximal end 201 and the distal end 203 of the expandable member 202 and extends radially outward from the instrument lumen 207 to an exterior of the expandable member. The inner surface of the inner layer 206 of the expandable member 202 maintains frictional contact with an instrument such as an endoscope 200. The inner layer 206 may be formed from a tube of a material, e.g., silicone, latex, or the like, which does not substantially change in dimension. The inner layer 206 is adhered to the outer layer 204 at the proximal 201 end of the expandable member 202. The inner layer 206 is also adhered to the outer layer 204 around the aperture 210. In some embodiments, the inner layer 206 is in the form of a tube having a lateral opening, with the material of the outer layer 204 extending into the aperture 210 and forming a sidewall of the aperture 210. The adhered surfaces may be achieved by an adhesive, a tape, flowed material, welding (e.g., laser, ultrasonic, hot jaw thermal, etc.), melt/re-melt flow processes, or the like. The adhered layers create a substantially tight fluid seal between the inner layer 206 and the outer layer 204 of the expandable member 202 such that an inflation fluid may be supplied through the inflation lumen of the fluid inlet 214 to transition the expandable member between a collapsed configuration like that of FIGS. 4A, 5A, and 6A and an expanded configuration like that of FIGS. 4B, 5B, and 6B. The inner layer 206 and outer layer 204 define the instrument lumen which can be pressurized by supplying fluid though the fluid inlet 214 to achieve the expanded configuration of FIGS. 4B, 5B, and 6B. The expandable member 202 in the expanded configuration is illustrated in an overall substantially cylindrical shape, but the expandable member 202 may be other shapes such as, e.g., ellipse, a sphere, a combination thereof, or the like. An endoscope 200 extending through the instrument lumen 207 of the expandable member 202 such that the distal end 212 of the endoscope 200 is in contact with the distal end 203 of the expandable member 202 may be used to examine a body lumen, as the inner layer 206 remains in frictional contact with the instrument. The working channel 208 of the endoscope 200 aligns with the aperture 210 of the expandable member 202. By transforming the expandable member 202 into the expanded configuration in a body lumen with the aperture 210 positioned toward the papilla, the expandable member 202 prevents movement of the endoscope 200 while access is made to the papilla.

The instrument accessory device 202 is illustrated in FIG. 3 such that it is configured to receive an endoscope 202 through the proximal end 201 toward the distal end 203. The expandable member 202 of the instrument accessory device 102 is shown expanded, which is the configuration where the instrument lumen 207 may slidingly receive the endoscope 200.

In various embodiments, an expandable member may have an expanded configuration and a collapsed configuration. An expandable member may comprise an outer layer forming an outer surface and an inner layer forming an inner surface. An outer layer may comprise a variety of compliant, semi-compliant, or non-compliant materials. These materials may comprise silicone, latex, polyurethane, rubber, isobutylene or the like. The thickness of a wall of the outer layer may vary with the material and may relate to the outer diameter of the outer layer in the collapsed and the expanded configuration. An inner layer may comprise a variety of semi-compliant, or non-compliant materials. These materials may comprise silicone, latex or the like. The thickness of a wall of the inner layer may vary with the material. The inner surface and outer surface may not expand to the same degree. An expandable member may be expanded and collapsed or otherwise stretched once or a plurality of times to increase its elasticity prior to use within a patient, which may improve a symmetrical inflation of the expandable member and may improve the centering mechanics of the expandable member. An expandable member may be expanded via a supply of an inflation fluid through one or more fluid inlets. The same fluid inlet may be used to expand and deflate the expandable member. Alternatively, a supply fluid inlet and a return fluid inlet may be intermittently or continuously used to circulate inflation fluid through an expandable member. A continuous flow of inflation fluid through a supply fluid inlet and a return fluid inlet may substantially maintain a desired pressure of the inflation fluid within the expandable member, or the inflation fluid may be heated and circulated to maintain a desired temperature with the expandable member.

In various embodiments, a vacuum may be applied by the instrument. The vacuum may pull the wall of the body lumen into the aperture. Where the aperture surrounds a duodenal papilla, the vacuum may draw open the papilla.

In various embodiments, the distal end of the instrument may or may not extend past the distal end of the instrument accessory device. If the distal end of the instrument does not extend past the distal end of the instrument accessory device, the expandable member may surround the distal end of the instrument.

In various embodiments, the inner surface may expand to a lesser degree than the outer surface. The inner and outer surfaces may comprise a polymeric material.

In various embodiments, the instrument accessory device may be disposable. In alternate embodiments, the instrument accessory device may be reusable.

In various embodiments, an inflation fluid supplied through a fluid inlet may include saline, water, $CO_2$, dilute contrast media, or the like.

In various embodiments, a method of performing an endoscopy may include placing an expandable instrument accessory device on an instrument. The instrument and instrument accessory device are together inserted into a patient. The expandable member can be expanded within the patient, dilating the patient's body lumen, e.g., the duodenum, the intestines, or the like. The instrument accessory device increases in diameter when the expandable member is expanded, inhibiting movement of both the expandable instrument accessory device and the instrument within the body lumen. Expanding the expandable member allows the instrument to remain still while using the instrument to examine other areas of the body. This can occur due to the outer diameter dilating the body lumen, preventing movement of the device. The instrument may be any device used to perform an endoscopy, e.g., ERCP or the like.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. An endoscopic system, comprising:
 a duodenoscope in fluid communication with a vacuum source; and
 an endoscope accessory device disposable about the duodenoscope, comprising:
 an expandable member having a proximal end, a distal end, a longitudinal axis, an inner layer having an inner surface defining an inner diameter of the expandable member, and an outer layer having an outer surface defining an outer diameter of the expandable member disposed about the inner layer, the inner surface defining an instrument lumen extending from the proximal end toward the distal end of the expandable member, the instrument lumen configured to receive an instrument therethrough;
 wherein the inner layer and the outer layer define inner and outer walls of a chamber that can be pressurized;
 wherein the expandable member comprises an aperture that extends radially outward from the instrument lumen to an exterior of the expandable member such that the instrument lumen is in fluid communication with the exterior of the expandable member via the aperture;
 wherein the expandable member is configured such that, when the device is disposed within a body lumen, a wall of the body lumen can be pulled into the aperture by a vacuum applied from the vacuum source by the duodenoscope; and
 wherein the instrument lumen of the expandable member is configured to slidingly receive at least a distal portion of the duodenoscope.

2. The system of claim 1, wherein the expandable member is configured to maintain frictional contact with the duodenoscope.

3. The system of claim 1, wherein the inner surface comprises a body.

4. The system of claim 1, wherein the system further comprises a vacuum source.

5. The system of claim 1, wherein when the expandable member is in an expanded condition, the endoscope is stabilized within a patient.

6. The system of claim 1, wherein the expandable member is pneumatically, electrically, or mechanically expandable.

* * * * *